United States Patent
Bekemeier et al.

(10) Patent No.: US 9,221,848 B2
(45) Date of Patent: Dec. 29, 2015

(54) METHOD OF FORMING AN MT-PROPYL SILOXANE RESIN

(75) Inventors: Thomas Daniel Bekemeier, Birch Run, MI (US); Gary Michael Wieber, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 146 days.

(21) Appl. No.: 13/979,170

(22) PCT Filed: May 1, 2012

(86) PCT No.: PCT/US2012/035935
§ 371 (c)(1),
(2), (4) Date: Jul. 11, 2013

(87) PCT Pub. No.: WO2012/151176
PCT Pub. Date: Nov. 8, 2012

(65) Prior Publication Data
US 2013/0289293 A1 Oct. 31, 2013

Related U.S. Application Data

(60) Provisional application No. 61/481,937, filed on May 3, 2011.

(51) Int. Cl.
| | | |
|---|---|---|
| C07F 7/02 | (2006.01) | |
| C07F 7/12 | (2006.01) | |
| C08G 77/04 | (2006.01) | |
| A61Q 19/00 | (2006.01) | |
| A61K 8/891 | (2006.01) | |
| C07F 7/08 | (2006.01) | |
| C07F 7/10 | (2006.01) | |
| C08G 77/06 | (2006.01) | |
| C08G 77/00 | (2006.01) | |

(52) U.S. Cl.
CPC . *C07F 7/12* (2013.01); *A61K 8/891* (2013.01); *A61Q 19/00* (2013.01); *C07F 7/0818* (2013.01); *C07F 7/10* (2013.01); *C08G 77/04* (2013.01); *C08G 77/06* (2013.01); *C08G 77/70* (2013.01)

(58) Field of Classification Search
CPC .......................................... C07F 7/12
USPC .......................................... 556/412
See application file for complete search history.

(56) References Cited

FOREIGN PATENT DOCUMENTS

| | | | |
|---|---|---|---|
| DE | 10059468 | 11/2001 | |
| FR | 2946872 | 12/2010 | |
| WO | 2005075542 | 8/2005 | |
| WO | 2009071662 | 6/2009 | |
| WO | WO 2010014352 A2 * | 2/2010 | ........... A61K 8/0229 |
| WO | 2010146147 | 12/2010 | |

* cited by examiner

*Primary Examiner* — Porfirio Nazario Gonzalez
*Assistant Examiner* — Kofi Adzamli
(74) *Attorney, Agent, or Firm* — John M. Olivo

(57) ABSTRACT

A method of forming an MT-propyl siloxane resin includes the steps of hydrolyzing propyl trichlorosilane in an excess of water to provide a T-propyl siloxane resin and capping the T-propyl siloxane resin formed from the hydrolysis of the propyl trichlorosilane with a silicon-containing M-group capping agent to form the MT-propyl siloxane resin. The MT-propyl siloxane resin is useful in a variety of personal care applications, and in particular, as an additive to personal care compositions.

8 Claims, No Drawings

METHOD OF FORMING AN MT-PROPYL SILOXANE RESIN

CROSS REFERENCE TO RELATED APPLICATIONS

This application is a U.S. national stage filing under 35 U.S.C. §371 of PCT Application No. PCT/US12/35935 filed on May 1, 2012, currently pending, which claims the benefit of U.S. Patent Application No. 61/481,937 filed May 3, 2011 under 35 U.S.C. §119 (e). PCT Application No. PCT/US12/35935 and U.S. Patent Application No. 61/481,937 are hereby incorporated by reference.

FIELD OF THE INVENTION

The present invention provides a method of forming an MT-propyl siloxane resin. More specifically, the present invention includes capping a T-propyl siloxane resin with a silicon-containing M-group capping agent to form the MT-propyl siloxane resin.

BACKGROUND OF THE INVENTION

Siloxane resins are important in many applications, such as personal care applications.

One particular subclass of siloxane resins, known as T-propyl siloxane resins, has found particular utility in personal care compositions, e.g. cosmetic formulations. However, T-propyl siloxane resins may be unstable, and their properties may gradually degrade over time. For example, the optical clarity of the T-propyl siloxane resin may degrade, thus leading to a personal care composition with a decreased level of optical clarity. The decrease in the optical clarity may also be accompanied by a molecular weight and viscosity increase, both of which are undesirable.

While the use of T-propyl siloxane resins in personal care applications has led to formulations with desirable properties, a need exists to alter the properties of the siloxane resins used in such formulations.

SUMMARY OF THE INVENTION AND ADVANTAGES

A method of forming an MT-propyl siloxane resin is provided. The method includes hydrolyzing propyl trichlorosilane in an excess of water to provide a T-propyl siloxane resin. The T-propyl siloxane resin includes at least 0.60 moles of $R^1SiO_{3/2}$ units per mole of silicon, where $R^1$ is a substituted or unsubstituted hydrocarbyl group having from 1 to 10 carbon atoms, an aryl group, a carbinol group, an amino group, or a sulfido group. At least 0.40 moles of the $R^1$ groups per mole of silicon are propyl groups. The method also includes capping the T-propyl siloxane resin formed from the hydrolysis of the propyl trichlorosilane with a silicon-containing M-group capping agent to form the MT-propyl siloxane resin. The silicon-containing M-group capping agent comprises at least 0.50 moles of monofunctional units per mole of silicon.

The method of forming the MT-propyl siloxane resin leads to an MT-propyl siloxane resin having the desirable properties of a T-propyl siloxane resin, but with a much greater level of stability. Furthermore, the inventors have discovered that personal care compositions containing the present MT-propyl siloxane resins have improved stability and optical clarity.

DETAILED DESCRIPTION OF THE INVENTION

A method of forming an MT-propyl siloxane resin is provided. The MT-propyl siloxane resin formed according to the method of this invention has utility in a wide variety of applications including, but not limited to, personal care applications. One application where the MT-propyl siloxane resin formed from this invention has particular utility is in personal care applications where personal care compositions, such as cosmetic formulations, are utilized. M, D, T, and Q units and nomenclature relying on such units are known in the art. For instance, the MT-propyl siloxane resin of this invention is a siloxane resin having, at least, M units and T units.

The method includes hydrolyzing propyl trichlorosilane in a molar excess of water to produce a T-propyl siloxane resin. The method further includes capping the T-propyl siloxane resin formed from hydrolyzing propyl trichlorosilane with a silicon-containing M-group capping agent to form the MT-propyl siloxane resin.

During the step of hydrolyzing propyl trichlorosilane in a molar excess of water, reaction temperatures are usually maintained from 0° C. to 80° C. or from 20° C. to 60° C. However, other reaction temperatures which enable hydrolysis are also contemplated, as will be appreciated by one of ordinary skill in the art. Typically, sufficient amounts of water are used in this step to provide greater than 0.9 moles of water per mole of Si in the resin, alternatively sufficient amounts of water are used in this step to provide a range of 0.9 moles up to 30 moles of water per mole of Si on the resin.

In certain embodiments, the silicon-containing M-group capping agent is added prior to or during the step of hydrolyzing propyl trichlorosilane. Alternatively, in other embodiments, the M-group capping agent may be provided after the step of hydrolyzing the propyl trichlorosilane (post-capping).

During the step of hydrolyzing propyl trichlorosilane, the propyl trichlorosilane and components other than the propyl trichlorosilane may be partially hydrolyzed where not all of the hydrolyzable groups in the propyl trichlorosilane or other components are hydrolyzed. As just one example, if the silicon-containing M-group capping agent is present during the step of hydrolyzing the propyl trichlorosilane and includes more than one hydrolyzable group, then the silicon-containing M-group capping agent may be partially hydrolyzed. Portions of the T-propyl siloxane resin may also be partially hydrolyzed after the T-propyl siloxane is formed.

The method includes hydrolyzing propyl trichlorosilane in a molar excess of water, as defined above. Alternatively, the propyl trichlorosilane can also be hydrolyzed in an excess of water and an organic solvent. In one embodiment, suitable organic solvents are those which are inert to the reactants during the hydrolysis. In another embodiment, a suitable organic solvent reacts with the reactants during the hydrolysis. For example, if the organic solvent includes methanol, the methanol may react with the propyl trichlorosilane. The organic solvent may comprise benzene, toluene, xylene, or similar aromatic hydrocarbons; hexane, heptane, isooctane, or similar linear or partially branched saturated hydrocarbons; and cyclohexane, or similar aliphatic hydrocarbons may be suitable. Excess organic solvent may be added to the mixture along with a co-solvent, such as an organic alcohol, to minimize any possibility of gelation during the reaction. Alcohols suitable for these purposes include, but are not limited to, methanol, ethanol, n-propyl alcohol, isopropyl alcohol, butanol, methoxy ethanol, ethoxy ethanol, or similar alcohols.

Furthermore, co-hydrolysis can be carried out by adding methyl trichlorosilane, dimethyldichlorosilane, phenyltrichlorosilane, or similar chlorosilanes and methyltrimethoxysilane, methyltriethoxysilane, methyltriisopropoxysilane, phenyltriethoxysilane, similar alkylalkoxysilanes, or hydrolyzates thereof to the reaction mixture.

If the hydrolysis of the propyl trichlorosilane is conducted in the presence of the organic solvent, and the alternative carrier solvent is more suited for the particular application for the MT-propyl siloxane resin, then the method may further comprise conducting a solvent-exchange between the organic solvent and the alternative carrier solvent. The step of conducting a solvent-exchange between the organic solvent and the alternative carrier solvent may include replacing the organic solvent used in the step of hydrolysis with an alternative carrier solvent. Typically, the alternative carrier solvent is one which is compatible with the other components in a personal care composition, and one which is suitable for human application. In contrast, the organic solvent used during the hydrolysis is not necessarily suitable for use in a personal care composition. The alternative carrier solvent may comprise isododecane, 2-butyloctanol, isohexadecane, $C_{12-15}$ alkyl benzoate, castor oil, hydrogenated palm oil, glycerin, or isopropyl palmitate. Alternatively, the alternative carrier solvent may comprise a cyclic siloxane, short chain siloxane, or some other form of hydrocarbon solvent. Short chain siloxane fluids are typically understood to mean those siloxanes having a molecular weight ($M_w$) ranging from 200 to 700. Notably, in personal care compositions, if the solvent-exchange step is conducted between the organic solvent and the alternative carrier solvent, then it is important that the alternative carrier solvent be compatible for human application. An aliphatic hydrocarbon solvent is typically used as the alternative carrier solvent.

The T-propyl siloxane resin may have a variety of configurations and characteristics. The T-propyl siloxane resin typically comprises at least 0.60 moles of $R^1SiO_{3/2}$ units per mole of silicon present in the siloxane resin, where $R^1$ is a substituted or unsubstituted hydrocarbyl group having from 1 to 10 carbon atoms, an aryl group, a carbinol group, an amino group, or a sulfido group, with the proviso that at least 0.40 of the $R^1$ groups per mole of silicon present in the siloxane resin are propyl groups.

Although the T-propyl siloxane resin comprises at least 0.60 moles of $R^1SiO_{3/2}$ units per mole of silicon, it is also contemplated that the T-propyl siloxane resin can also comprise at least 0.70, 0.80, 0.90, 0.95, 0.99, or 1.0 moles of $R^1SiO_{3/2}$ units per mole of silicon present in the siloxane resin. As also indicated above, the T-propyl siloxane resin is also characterized by the proviso that at least 0.40 moles of the $R^1$ groups per mole of silicon are propyl groups. Typically, at least 0.50, 0.60, 0.70, 0.80, 0.90, 0.95, 0.99, or 1.0 moles of $R^1$ groups per mole of silicon are propyl groups. In another embodiment, one mole of $R^1$ groups per mole of silicon are propyl groups. It is also contemplated that the T-propyl siloxane resin comprises M-units in addition to the T units mentioned above.

The T-propyl siloxane resin typically comprises residual silanol groups prior to capping with the silicon-containing M-group capping agent. In one configuration, the T-propyl siloxane resin comprises from 0.20 to 1.20 moles of silanol groups per mole of silicon present in the siloxane resin before being capped with the silicon-containing M-group capping agent. Alternatively, the T-propyl siloxane resin comprises from 0.30 to 0.70 moles of silanol groups per mole of silicon, or from 0.35 to 0.50 moles of silanol groups per mole of silicon before being capped with the silicon-containing M-group capping agent.

The silicon-containing M-group capping agent comprises at least 0.50 moles of monofunctional units per mole of silicon. In certain embodiments, the silicon-containing M-group capping agent may comprise at least one $R_3SiO_{1/2}$ unit, at least one disiloxane, or at least one disilazane.

In one embodiment, the silicon-containing M-group capping agent comprises a compound having the following average formula:

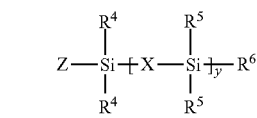

In this formula, Z is Cl, an alkoxy group having from 1 to 10 carbons, or a substituted or unsubstituted hydrocarbyl group having from 1 to 10 carbon atoms; $R^4$, $R^5$, and $R^6$ is each independently a substituted or unsubstituted hydrocarbyl groups having from 1 to 10 carbon atoms; X is O or NH, and y ranges from 0 to 10. In one specific embodiment, y ranges from 0 to 1. Although certain M-group capping agents are enumerated throughout this disclosure, other capping agents are also contemplated for use with the method described as will be appreciated by one of ordinary skill in the art. Alternatively, hydrolyzates of the compounds set forth above may be utilized as the silicon-containing M-group capping agent.

The silicon-containing M-group capping agent may be a chlorosilane, an alkoxysilane, a disiloxane, or a disilazane. The silicon-containing M-group capping agent may comprise a monofunctional silane, a siloxane, or a silazane. Suitable monofunctional silanes include, for example, triorganosilanes, such as halo-, alkoxy-, and carboxy-triorganosilanes. More particularly, specific examples of the silicon-containing M-group capping agent include trimethylchlorosilane, trimethylmethoxysilane, hexamethyldisiloxane, diphenylmethylmethoxysilane, dimethylphenylmethoxysilane, diphenylmethylchorosilane, dimethylphenylchlorosilane, hexamethyldisilazane, and hydrolyzates thereof. In one embodiment, the silicon-containing M-group capping agent comprises trimethylchlorosilane. Mixtures of silicon-containing M-group capping agents may also be used if desired.

The silicon-containing M-group capping agent may be added at various times during the formation of the MT-propyl siloxane resin, such as before, during or after the step of hydrolyzing propyl trichlorosilane. Thus, the silicon-containing M-group capping agent may partially hydrolyze before capping of the T-propyl siloxane resin.

If the silicon-containing M-group capping agent is added prior to or during the step of hydrolyzing propyl trichlorosilane, the amount of silicon-containing M-group capping agent may range from 0.01 to 0.90 moles of silicon-containing M-group capping agent per mole of propyl trichlorosilane provided. Alternatively, the amount of silicon-containing M-group capping agent may range from 0.10 to 0.60, or 0.15 to 0.50 moles of silicon-containing M-group capping agent per mole of propyl trichlorosilane provided.

If the silicon-containing M-group capping agent is provided after the step of hydrolyzing propyl trichlorosilane, the amount of silicon-containing M-group capping agent may range from 0.01 to 0.50 moles of silicon-containing M-group capping agent per mole of T-propyl siloxane resin. Alternatively, the amount of the silicon-containing M-group capping agent may range from 0.01 to 0.40, or from 0.01 to 0.30, or from 0.01 to 0.20 moles of silicon-containing M-group capping agent per mole of T-propyl siloxane resin. In such an embodiment, the value of a (the mole fraction of M units) is less than 0.20. Alternatively, the value of a in such an embodiment, may range from 0.05 to less than 0.20, or from 0.05 to 0.15, or from 0.10 to 0.15.

In one embodiment where solvent-exchange is utilized, the silicon-containing M-group capping agent is added before the step of conducting the solvent-exchange. In another configuration, the silicon-containing M-group capping agent is added during or after the step of conducting the solvent-exchange with the organic solvent to the alternative carrier solvent.

Although the method is not limited to any particular theory, the silicon-containing M-group capping agent reacts with silanol groups of the T-propyl siloxane resin. Addition and reaction of the silicon-containing M-group capping agent is typically carried out at a temperature ranging from 20° C. to 150° C., or from 40° C. to 120° C. After addition of the silicon-containing M-group capping agent, the mixture is heated for a time period ranging from 5 minutes to 480 minutes, or from 30 minutes to 180 minutes, to complete the capping step.

After capping of the T-propyl siloxane resin, the MT-propyl siloxane resin typically comprises from 0.05 to 0.40 moles of silanol groups per mole of silicon present in the siloxane resin, from 0.10 to 0.35 moles of silanol groups per mole of silicon, or from 0.15 to 0.35 moles of silanol groups per mole of silicon.

In an alternative embodiment, the MT-propyl siloxane resin has the average formula $(R^2_3SiO_{1/2})_a$ $(R^1SiO_{3/2})_c$, wherein a is less than 0.20, and c ranges from 0.80 to less than 1, with the proviso that a+c=1. It is also contemplated that a ranges from 0.05 to less than 0.20, or from 0.05 to 0.15, and c ranges from 0.80 to 0.95, or from 0.80 to 0.90 with the proviso that a+c=1.

An equilibration catalyst may be added to the propyl trichlorosilane if desired. The equilibration catalyst may include, but is not limited to, an acid, a base, or an alternative catalyst, as will be appreciated by one of ordinary skill in the art.

A polyorganosiloxane can optionally be included in the method of the present disclosure. Polyorganosiloxanes which may be added include D units and T units. The polyorganosiloxane can be added to introduce various D and T units into the MT propyl siloxane resins to alter the properties of the resulting siloxane resins. The structure or formula of the polyorganosiloxane is not restrictive, providing the polyorganosiloxane contains some measurable quantity of D units or T units, and the total amount of polyorganosiloxane added to the reaction of T-propyl siloxane resin and the M-capping agent does not provide more than 0.50 moles of D or T units per mole of silicon into the reaction mixture.

The polyorganosiloxane can be selected from any of the fluid, gum, or resinous silicones known in the art containing D or T units, or combinations thereof. The D units typically contain methyl or phenyl substituent groups, or any combinations thereof. The T units typically contain methyl or phenyl substituent groups, or any combinations thereof. The polyorganosiloxane can be a linear polydiorganosiloxane fluid having a viscosity of 10-1000 cS (mm$^2$/s) at 25° C. Typically the polydiorganosiloxane fluid is polydimethylsiloxane, or alternatively a polymethylphenylsiloxane. The polyorganosiloxane can also be an organosilsesquioxane. The organosilsesquioxane resin typically is a methylsilsesquioxane resin or a phenylsilsesquioxane resin.

Any individual D, T or Q siloxane units of the siloxane resins can also contain a hydroxyl group and/or alkoxy group. Such siloxane units containing hydroxyl and/or alkoxy groups are commonly found in siloxane resins.

The T-propyl siloxane resin described herein may be produced with a batch, semi-continuous, or continuous process. In certain embodiments, the T-propyl siloxane resin is produced in a continuous process.

An MT-propyl siloxane resin comprising the reaction product of a T-propyl siloxane resin and a silicon-containing M-group capping agent is also provided. The silicon-containing M-group capping agent comprises at least 0.50 moles of monofunctional units per mole of silicon. The T-propyl siloxane comprising at least 0.60 moles of $R^1SiO_{3/2}$ units per mole of silicon, where $R^1$ is a substituted or unsubstituted hydrocarbyl group having from 1 to 10 carbon atoms, an aryl group, a carbinol group, an amino group, or a sulfido group. In the T-propyl siloxane resin, at least 0.40 moles of the $R^1$ groups per mole of silicon are propyl groups. It is contemplated that this reaction product and reactants can vary in accordance with the disclosure provided throughout.

In another embodiment, an MT-propyl siloxane resin that comprises the units (i) $(R^2_3SiO_{1/2})_a$, (ii) $(R^3_2SiO_{2/2})_b$, (iii) $(R^1SiO_{3/2})_c$, and (iv) $(SiO_{4/2})_d$ is provided. As described immediately below, the amount of each unit present in the MT propyl siloxane resin can be expressed as a mole fraction (a, b, c, or d) of the total number of moles of all $(R^2_3SiO_{1/2})_a$, $(R^3_2SiO_{2/2})_b$, $(R^1SiO_{3/2})_c$, and $(SiO_{4/2})_d$ units.

The value of a (the mole fraction of M units is typically less than 0.20. Alternatively, the value of a may range from 0.05 to less than 0.20, or from 0.05 to 0.15, or from 0.10 to 0.15. The value of b (the mole fraction of D units) typically ranges from 0 to 0.30, or from 0 to 0.20, or from 0 to 0.10. The value of c (the mole fraction of T units) is typically a value greater than 0.60, 0.70, 0.80, 0.90, or 0.95. Alternatively, the value of c is greater than the value of a, greater than the value of b, and greater than the value of d. It is contemplated that c is the single most numerous component. The value of d (the mole fraction of Q units) typically ranges from 0 to 0.50, from 0 to 0.30, or from 0 to 0.10. Thus, as illustrated by the above formula, the MT propyl siloxane resins can be free of D and Q units, or alternatively can contain various amounts of either. In the above formula, the value of a+b+c+d=1.

The R', $R^2$, and $R^3$ in the MT propyl siloxane resin is each independently selected from a substituted or unsubstituted hydrocarbyl group having from 1 to 10 carbon atoms, an aryl group, a carbinol group, an amino group, and a sulfido group. Exemplary unsubstituted hydrocarbyl groups are illustrated by methyl, ethyl, propyl, butyl, pentyl, hexyl, and octyl. Exemplary aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl.

For the purposes of this disclosure, a carbinol group is defined as any group containing at least one carbon-bonded hydroxyl (COH) radical. Thus, the carbinol groups may contain more than one COH radical. The carbinol group, if free of aryl groups, has at least 3 carbon atoms. An aryl containing carbinol group may have at least 6 carbon atoms. A carbinol group free of aryl groups having at least 3 carbon atoms is illustrated by groups having the formula $R^4OH$, where $R^4$ is a divalent hydrocarbon radical having at least 3 carbon atoms or is a divalent hydrocarbonoxy radical having at least 3 carbon atoms. The group $R^4$ is illustrated by alkylene radicals such as $(CH_2)_x$, $CH_2CH(CH_3)$, $CH_2CH(CH_3)CH_2$, $CH_2CH_2CH(CH_2CH_3)CH_2CH_2CH_2$, and $OCH(CH_3)(CH_2)_x$, where x has a value of 1 to 10.

The aryl-containing carbinol group having at least 6 carbon atoms is illustrated by groups having the formula $R^5OH$, where $R^5$ is an arylene radical such as $—(CH_2)_xC_6H_4$, $CH_2CH(CH_3)(CH_2)_xC_6H_4$, $(CH_2)_xC_6H_4(CH_2)_x$, where x has a value of 1 to 10. The aryl containing carbinol groups typically have from 6 to 14 atoms.

The amino group is illustrated by groups having the formula $R^6NH_2$ or $R^6NHR^7NH_2$, where $R^6$ is a divalent hydrocarbon radical having at least 2 carbon atoms and $R^7$ is a divalent hydrocarbon radical having at least 2 carbon atoms. The group $R^6$ is typically an alkylene radical having from 2 to 20 carbon atoms. $R^6$ is illustrated by ethylene, propylene, butylene, iso-butylene, pentamethylene, hexamethylene, 3-ethyl-hexamethylene, octamethylene, and decamethylene.

$R^7$ is typically an alkylene radical having from 2 to 20 carbon atoms. $R^7$ is illustrated by ethylene, propylene, $CH_2CHCH_3$, butylene, —$CH2CH(CH_3)CH_2$—, pentamethylene, hexamethylene, 3-ethyl-hexamethylene, octamethylene, and decamethylene.

Typical amino groups are: $CH_2CH_2CH_2NH_2$, $CH_2(CH_3)CHCH_2(H)NCH_3$, $H_2CH_2NHCH_2CH_2NH_2$, $CH_2CH_2NH_2$, $CH_2CH_2NHCH_3$, $CH_2CH_2CH_2CH_2NH_2$, $(CH_2CH_2NH)_3H$, and $CH_2CH_2NHCH_2CH_2NHC_4H_9$.

The molecular weights of the MT-propyl siloxane resins are not particularly restricted, but the weight average molecular weight ($M_w$) may range from 2,000 to 100,000, or from 5,000 to 60,000, or from 5,000 to 30,000.

As will be understood, the MT-propyl siloxane resin can be formed in accordance with the methods described above or in accordance with other methods as is understood by those of ordinary skill in the art.

As indicated above, the MT-propyl resin of the present disclosure is useful in a variety of personal care applications. Thus, a personal care composition comprising the MT-propyl siloxane resin disclosed throughout the subject disclosure is contemplated.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. It is intended that the invention not be limited to the particular embodiment disclosed as the best mode contemplated for carrying out this invention, but that the invention will include all embodiments falling within the scope of the appended claims.

What is claimed is:

1. A method of forming an MT-propyl siloxane resin having at least 0.60 moles of $R^1SiO_{3/2}$ units per mole of silicon, wherein $R^1$ is a substituted or unsubstituted hydrocarbyl group having from 1 to 10 carbon atoms, an aryl group, a carbinol group, an amino group, or a sulfido group, and with the proviso that at least 0.40 moles of the $R^1$ groups per mole of silicon are propyl groups, said method comprising:
    hydrolyzing propyl trichlorosilane in an excess of water to provide a T-propyl siloxane resin;
    capping the T-propyl siloxane resin formed from hydrolyzing propyl trichlorosilane with a silicon-containing M-group capping agent to form the MT-propyl siloxane resin, wherein the silicon-containing M-group capping agent comprises at least 0.50 moles of monofunctional units per mole of silicon, wherein the silicon-containing M-group capping agent is selected from triorganosilanes, halotriorganosilanes, alkoxytriorganosilanes, carboxytriorganosilanes, chlorosilanes, alkoxysilanes, disiloxanes, disilazanes, and compounds having average formula:

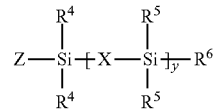

wherein Z is Cl, an alkoxy group having from 1 to 10 carbons, or a substituted or unsubstituted hydrocarbyl group having from 1 to 10 carbon atoms, and each $R^4$, $R^5$, and $R^6$ is independently a substituted or unsubstituted hydrocarbyl group having from 1 to 10 carbon atoms; X is O or NH, and y ranges from 0 to 10; or hydrolyzate thereof, wherein the MT-propyl siloxane resin has the average formula:

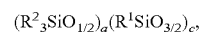

wherein:
    a is less than 0.20, and 'c' ranges from 0.80 to less than 1, with the proviso that a+c=1.

2. The method of forming an MT-propyl siloxane resin of claim 1, wherein the MT-propyl siloxane resin comprises from 0.05 to 0.40 moles of silanol groups per mole of silicon.

3. The method of forming an MT-propyl siloxane resin of claim 1, wherein the step of hydrolyzing propyl trichlorosilane is conducted in the presence of an organic solvent, and the method further comprises the step of conducting a solvent-exchange between the organic solvent and an alternative carrier solvent.

4. The method of forming an MT-propyl siloxane resin of claim 1, wherein the silicon-containing M-group capping agent comprises a compound having the following average formula:

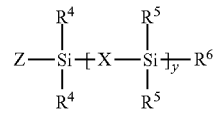

wherein Z is Cl, an alkoxy group having from 1 to 10 carbons, or a substituted or unsubstituted hydrocarbyl group having from 1 to 10 carbon atoms, and each $R^4$, $R^5$, and $R^6$ is independently a substituted or unsubstituted hydrocarbyl group having from 1 to 10 carbon atoms; X is O or NH, and y ranges from 0 to 10; or hydrolyzate thereof.

5. The method of forming an MT-propyl siloxane resin of claim 1, wherein the silicon-containing M-group capping agent comprises trimethylchlorosilane or a hydrolyzate thereof.

6. The method of forming an MT-propyl siloxane resin of claim 1, wherein the silicon-containing M-group capping agent is provided before the step of hydrolyzing propyl trichlorosilane.

7. An MT-propyl siloxane resin, wherein the MT-propyl siloxane resin has the average formula:

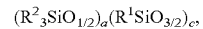

wherein:
    a is less than 0.20, and c ranges from 0.80 to less than 1, with the proviso that a+c=1.

8. The MT-propyl siloxane resin of claim 7, wherein the MT-propyl siloxane resin comprises from 0.05 to 0.40 moles of silanol groups per mole of silicon.

* * * * *